(12) United States Patent
Stayman et al.

(10) Patent No.: US 8,055,049 B2
(45) Date of Patent: Nov. 8, 2011

(54) MOTION CORRECTION FOR CT USING MARKER PROJECTIONS

(75) Inventors: Joseph Webster Stayman, Ann Arbor, MI (US); Matt Jacobson, Ann Arbor, MI (US)

(73) Assignee: Xoran Technologies, Inc., Ann Arbor, MI (US)

( * ) Notice: Subject to any disclaimer, the term of this patent is extended or adjusted under 35 U.S.C. 154(b) by 782 days.

(21) Appl. No.: 12/174,855

(22) Filed: Jul. 17, 2008

(65) Prior Publication Data

US 2009/0022266 A1 Jan. 22, 2009

Related U.S. Application Data

(60) Provisional application No. 60/950,405, filed on Jul. 18, 2007, provisional application No. 61/027,886, filed on Feb. 12, 2008.

(51) Int. Cl.
*G06K 9/00* (2006.01)
(52) U.S. Cl. ............................................. 382/131; 378/8
(58) Field of Classification Search ................... 382/107, 382/128, 130–132, 275; 378/4–20, 62, 98.11, 378/98.12, 207
See application file for complete search history.

(56) References Cited

U.S. PATENT DOCUMENTS

| | | | |
|---|---|---|---|
| 5,982,915 | A | 11/1999 | Doi et al. |
| 6,122,541 | A | 9/2000 | Cosman et al. |
| 6,490,475 | B1 | 12/2002 | Seeley et al. |
| 6,496,560 | B1 | 12/2002 | Lin et al. |
| 6,553,132 | B1 | 4/2003 | Thesen |
| 6,973,202 | B2 | 12/2005 | Mostafavi |
| 6,990,368 | B2 | 1/2006 | Simon et al. |
| 7,012,603 | B2 | 3/2006 | Chen et al. |
| 7,110,614 | B2 | 9/2006 | Launay et al. |
| 7,154,987 | B2 | 12/2006 | Rubin et al. |
| 7,215,800 | B2 | 5/2007 | Allouche |
| 7,221,728 | B2 | 5/2007 | Edic et al. |
| 2004/0136490 | A1 | 7/2004 | Edic et al. |

*Primary Examiner* — Courtney Thomas
(74) *Attorney, Agent, or Firm* — Carlson, Gaskey & Olds, P.C.

(57) ABSTRACT

A method of correcting for motion of a patient during a CT scan includes observing positions of radio-opaque markers in a series of two dimensional x-ray projections taken by a scanner. The markers are positioned on a patient in a fixed and rigid relationship, a CT scan is performed to obtain a three dimensional CT image, and an actual projected position of each of the markers in each two dimensional projection is determined. A motion data set is obtained based on the actual projected positions of the plurality of the markers. A final three dimensional CT image is reconstructed employing the motion data set.

31 Claims, 7 Drawing Sheets

MOTION CORRECTION FOR CT USING MARKER PROJECTIONS

REFERENCE TO RELATED APPLICATION

The application claims priority to U.S. Provisional Application No. 60/950,405 filed on Jul. 18, 2007 and U.S. Provisional Application No. 61/027,886 filed on Feb. 12, 2008.

BACKGROUND OF THE INVENTION

The present invention relates generally to a method for correcting for motion of a patient during a computed tomography (CT) scan.

A CT scanner includes a gantry that supports and houses an x-ray source that generates x-rays and a complementary flat-panel detector. The CT scanner obtains a plurality of x-ray projections at a plurality of rotational positions. The CT scanner includes a computer that generates a three dimensional CT image from the plurality of x-ray projections.

The three dimensional CT image can be employed in the medical field to diagnose and treat medical conditions. If the patient moves during a CT scan, the resulting three dimensional CT image can be affected.

SUMMARY OF THE INVENTION

A set of markers that are radio-opaque (i.e., are relatively opaque to x-rays) are attached to a patient's head. A CT scanner takes a CT scan of the patient to capture two dimensional x-ray projections. A computer generates a three dimensional CT image from the two dimensional x-ray projections.

The computer searches the three dimensional CT image for any motion-blurred markers, and the locations of the motion-blurred markers are stored on the computer. The motion-blurred markers are deleted from the three dimensional CT image to generate a new three dimensional CT image. The new three dimensional CT image is used to generate a set of simulated two dimensional x-ray projections of the anatomy of the patient. The simulated two dimensional x-ray projections are subtracted from the two dimensional x-ray projections to produce a set of two dimensional x-ray projections that show only the markers.

An actual position of each of the plurality of markers in the new set of two dimensional x-ray projections showing only the markers is then determined. A motion data set is obtained based on the actual projected positions of the markers. A final three dimensional CT image is then reconstructured employing the motion data set.

DETAILED DESCRIPTION OF THE PREFERRED EMBODIMENT

Figure 1:
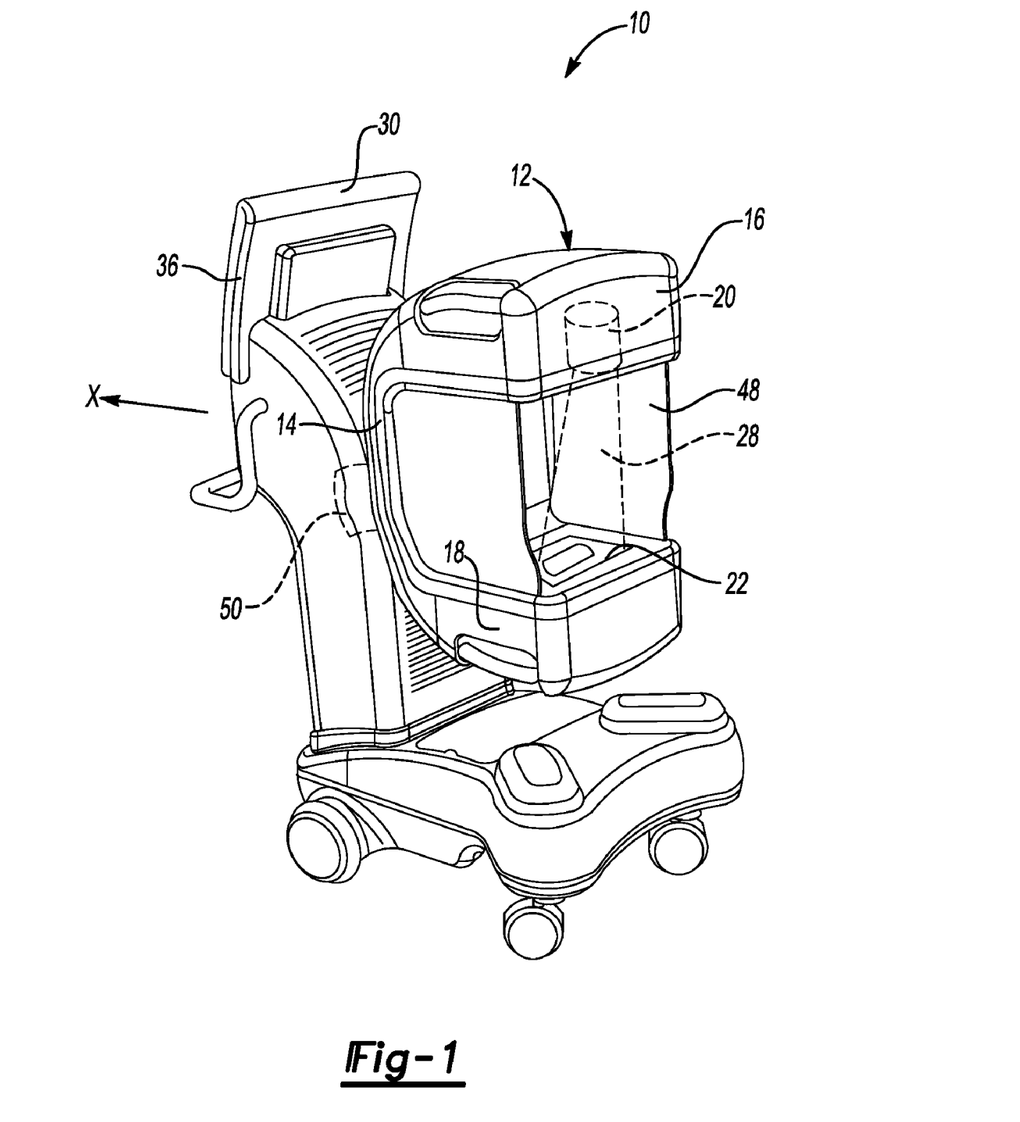
FIG. 1 schematically illustrates a first embodiment CT scanner.

FIG. 1 illustrates a CT scanner 10 including a gantry 12 that supports and houses components of the CT scanner 10. Suitable CT scanners 10 are known. In one example, the gantry 12 includes a cross-bar section 14, and a first arm 16 and a second arm 18 each extend substantially perpendicularly from opposing ends of the cross-bar section 14 to form the c-shaped gantry 12. The first arm 16 houses an x-ray source 20 that generate x-rays 28. In one example, the x-ray source 20 is a cone-beam x-ray source. The second arm 18 houses a complementary flat-panel detector 22 spaced apart from the x-ray source 20. The x-rays 28 are directed toward the detector 22 which includes a converter (not shown) that converts the x-rays 28 from the x-ray source 20 to visible light and an array of photodetectors behind the converter to create an image. As the gantry 12 rotates about the patient P, the detector 22 takes a plurality of x-ray projections at a plurality of rotational positions. Various configurations and types of x-ray sources 20 and detectors 22 can be utilized, and the invention is largely independent of the specific technology used for the CT scanner 10.

Figure 2:
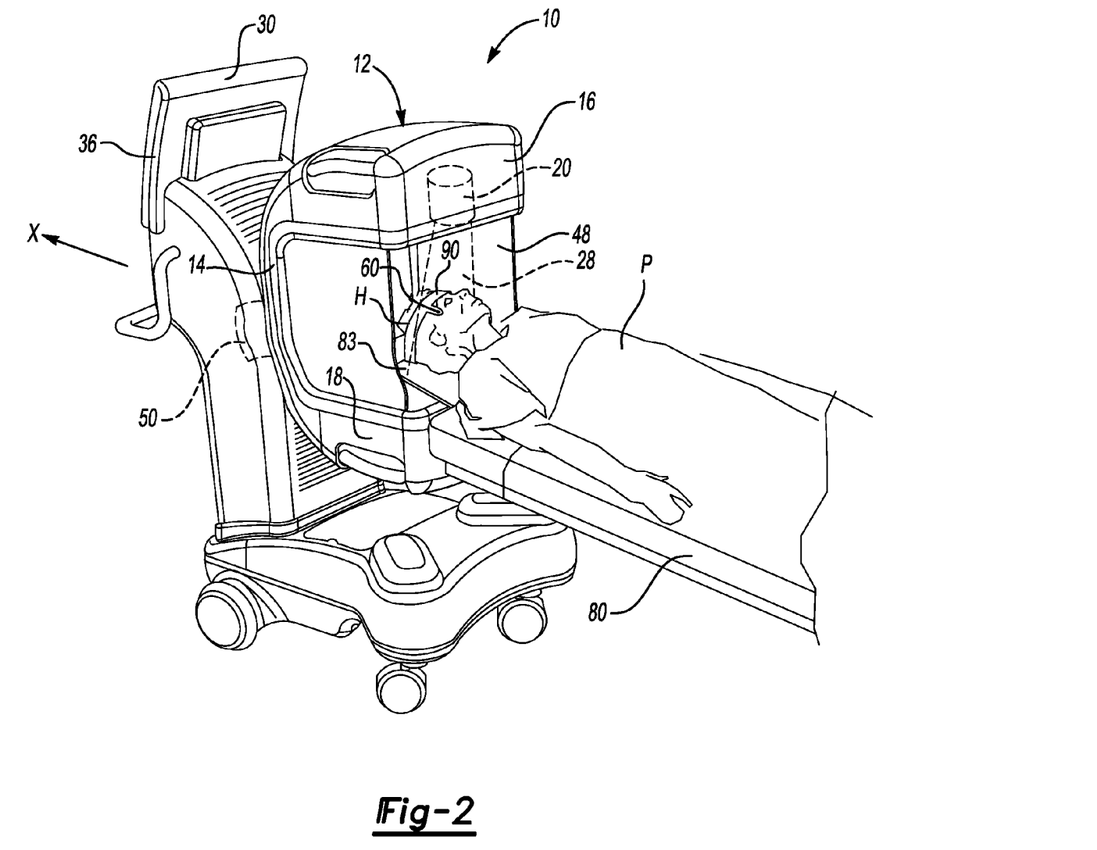
FIG. 2 illustrates the CT scanner of FIG. 1 with a part of a patient received in the CT scanner.
Figure 3:
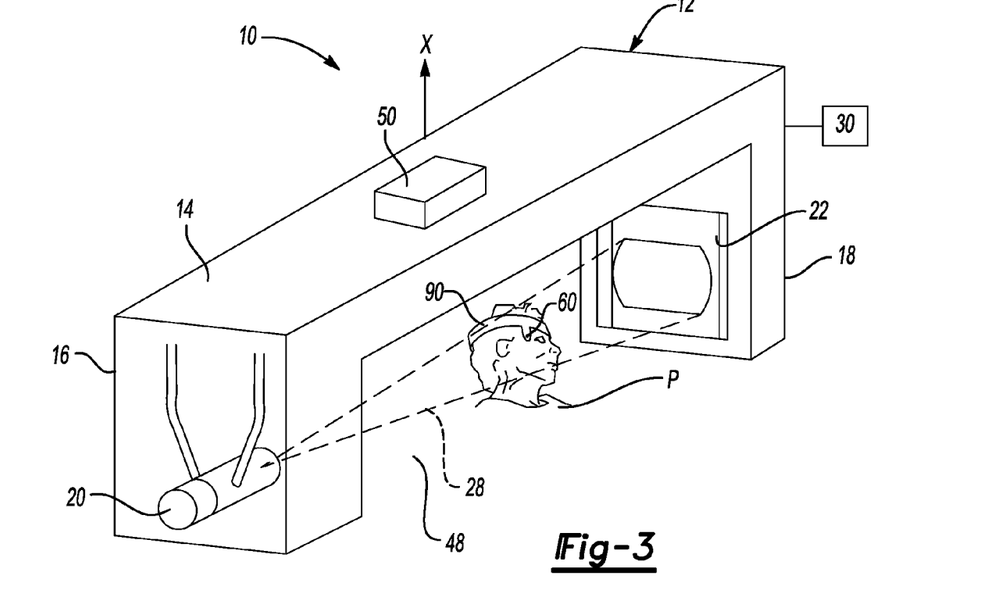
FIG. 3 illustrates a second embodiment of the CT scanner.

FIG. 2 illustrates the CT scanner 10 with a part of the patient P received in a space 48 between the first arm 16 and the second arm 18. A motor 50 rotates the gantry 12 about an axis of rotation X to obtain a plurality of x-ray projections of the patient P at the plurality of rotational positions. The axis of rotation X is positioned between the x-ray source 20 and the detector 22. The gantry 12 can be rotated approximately slightly more than 360 degrees about the axis of rotation X. In one example, as shown in FIGS. 1 and 2, the axis of rotation X is substantially horizontal. In this example, the patient P is typically lying down on a table 70. Alternatively, as shown in FIG. 3, the axis of rotation X is substantially vertical. Typically, in this example, the patient P is sitting upright.

Figure 4:
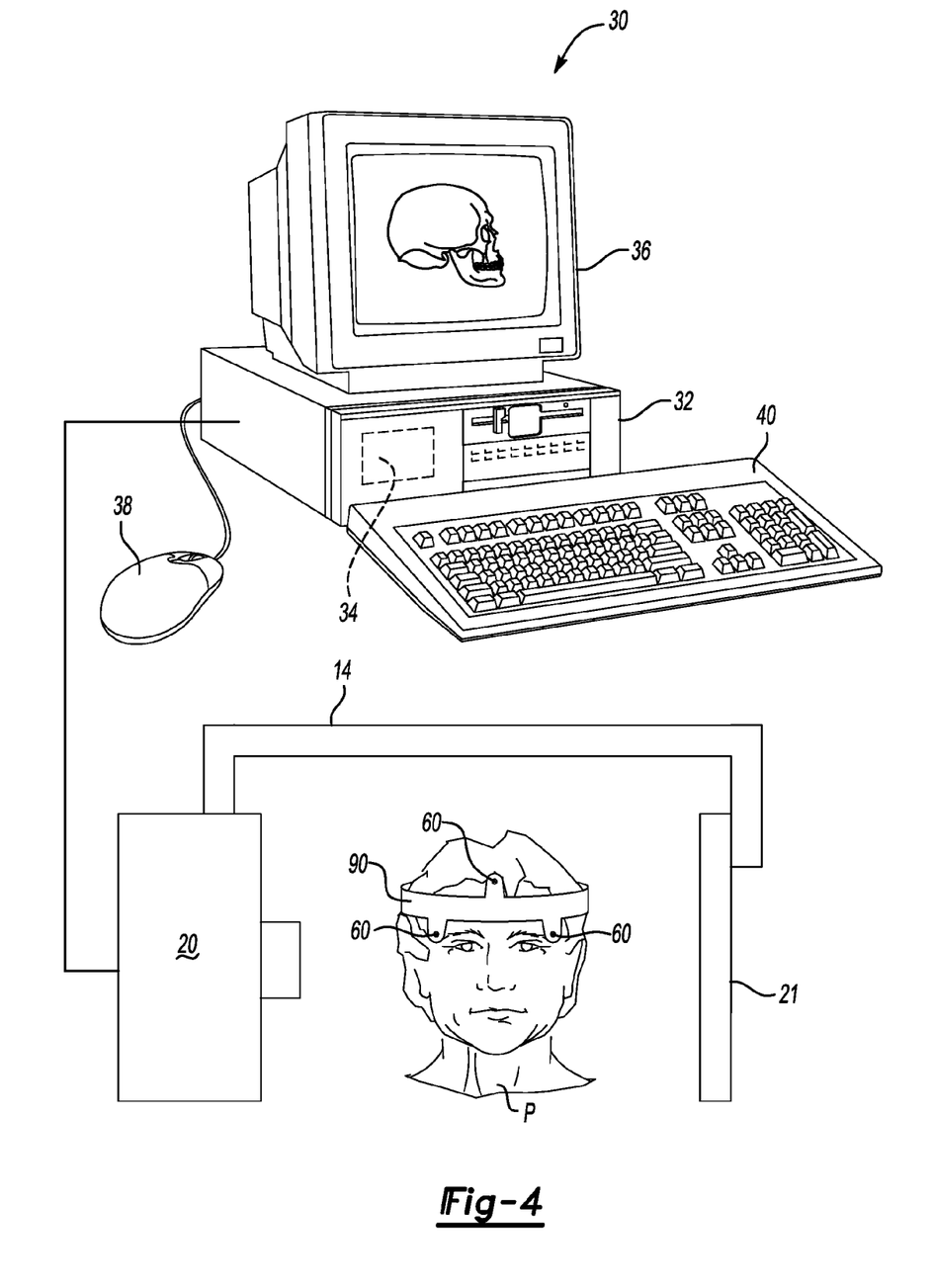
FIG. 4 illustrates a computer employed with the CT scanner.

As shown schematically in FIG. 4, the CT scanner 10 further includes a computer 30 having a microprocessor or CPU 32, a storage 34 (memory, hard drive, optical, and/or magnetic, etc), a display 36, a mouse 38, a keyboard 40 and other hardware and software for performing the functions described herein. The computer 30 powers and controls the x-ray source 20 and the motor 50. The plurality of x-ray projections taken by the detector 22 are sent to the computer 30. The computer 30 generates a three-dimensional CT image from the plurality of x-ray projections utilizing any known techniques and algorithms. The three-dimensional CT image is stored on the storage 34 of the computer 30 and can be displayed on the display 36 for viewing.

Figure 5:
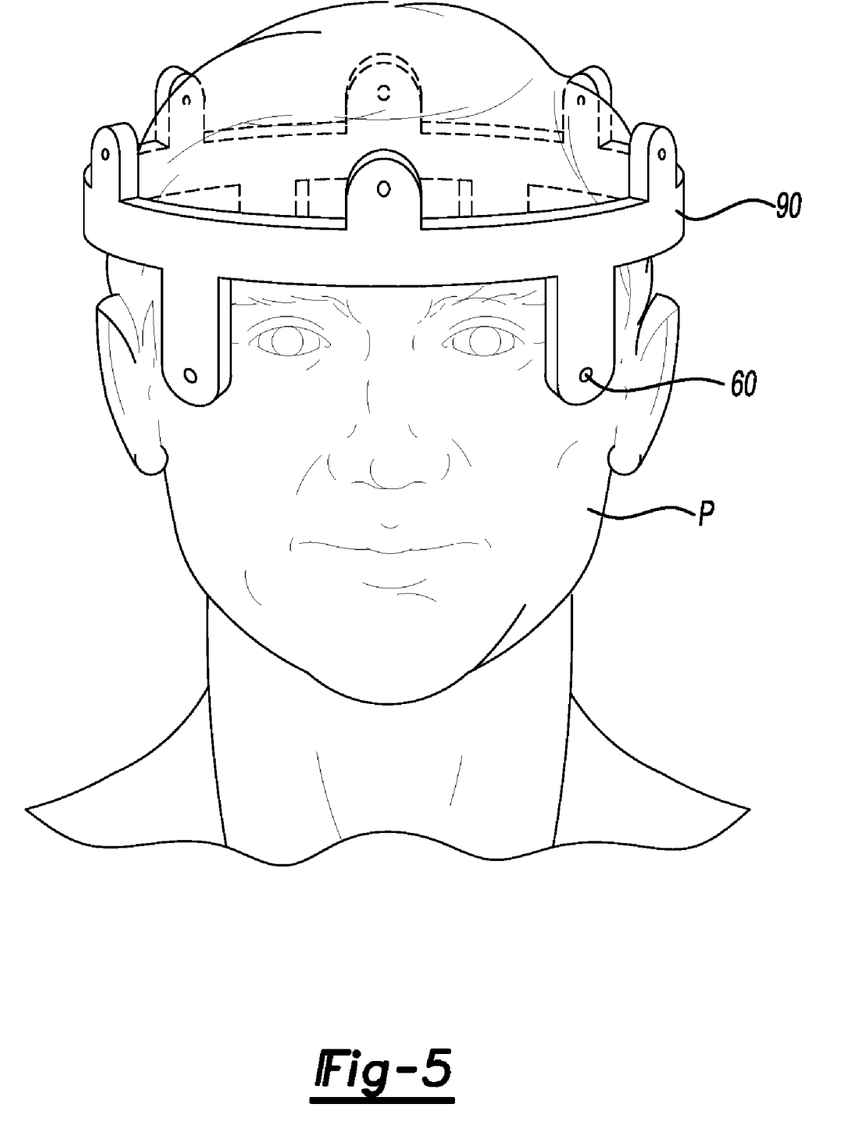
FIG. 5 illustrates a head gear including markers positioned on the patient.

As shown in FIG. 5, a head gear 90 including a plurality of radio-dense or radio-opaque markers 60 is positioned on a head of the patient P. The head gear 90 is designed to fit a variety of different head sizes. The markers 60 can be a plurality of ball bearings or BBs. The markers 60 remain in a fixed position relative to each other once attached to the head of the patient P. The position of the markers 60 is important in determining motion of the patient P during a CT scan. In one example, there are more than three markers 60 on the head gear 90.

Figure 6:
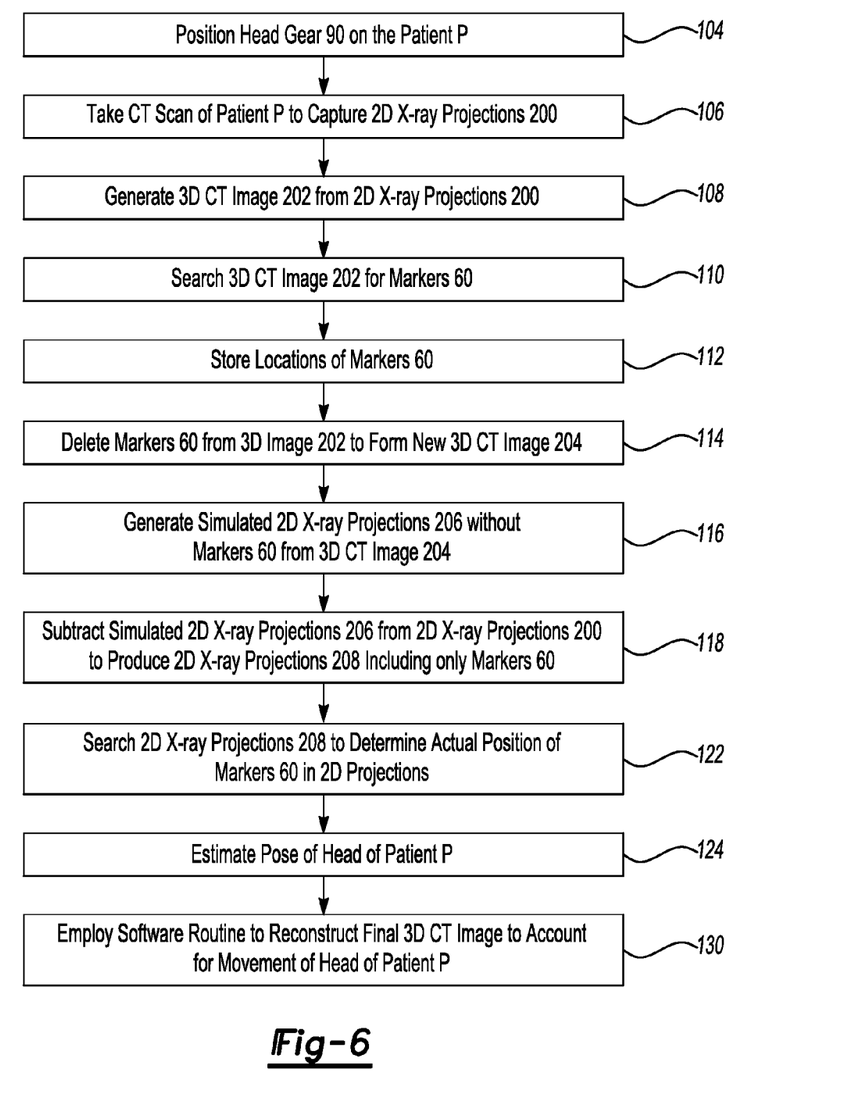
FIG. 6 illustrates a flowchart of a process of motion correction of a CT scan.
Figure 7:
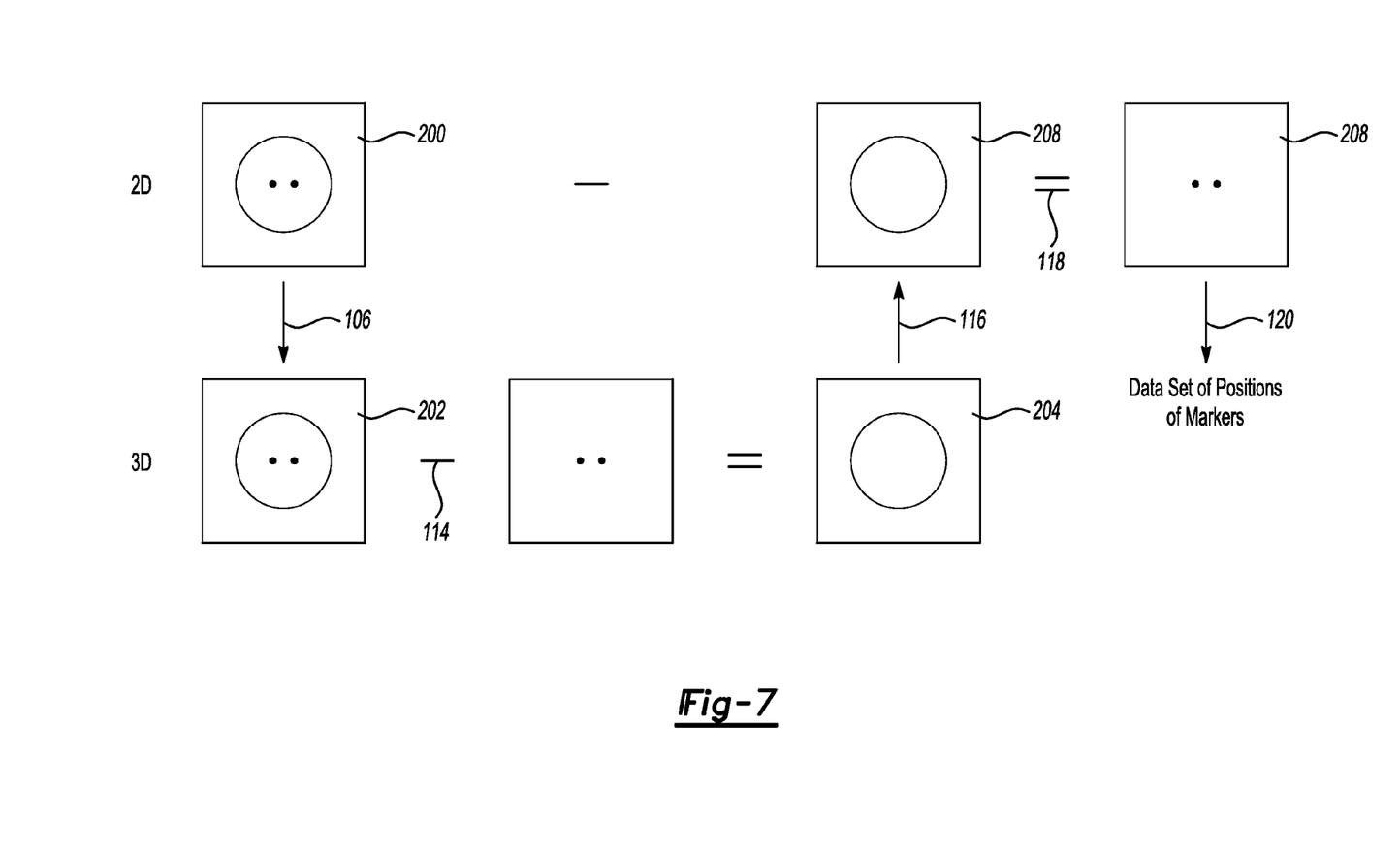
FIG. 7 illustrates a method of manipulating CT images.

FIG. 6 shows a flowchart of the method of measuring and correcting for the motion of the patient P that occurs during the CT scan. FIG. 7 illustrates a process of image manipulation to measure the motion. The computer 30 performs the below described steps.

At step 104, before a CT scan, the head gear 90 is positioned on the patient P. At step 106, the CT scanner 10 takes a CT scan of the head of the patient P to capture two dimensional x-ray projections 200. At step 108, the computer 30 generates a three dimensional CT image 202 from the two dimensional x-ray projections 200, ignoring any motion of the patient P.

At step 110, the computer 30 searches the three dimensional CT image 202 for any motion-blurred markers 60. The computer 30 can search for the markers 60 by searching for areas where the intensity levels are above a predetermined threshold. At step 112, the locations of the motion-blurred markers 60 are stored in the computer 30. Then, at step 114, the motion-blurred markers 60 are deleted from the three dimensional CT image 202 to generate a new three dimensional CT image 204 of only the patient P (without the markers 60).

In step 116, the new three dimensional CT image 204 is used to generate a set of simulated two dimensional x-ray projections 206 of only the anatomy of the patient P (without the markers 60). In step 118, the simulated two dimensional x-ray projections 206 are subtracted from the two dimensional x-ray projections 200 to produce a set of two dimensional x-ray projections 208 that essentially show only the markers 60. That is, each simulated two dimensional x-ray projection 206 is subtracted from the corresponding two dimensional x-ray projection 200. The anatomy of the patient P is faint, allowing the markers 60 to be easily spotted.

In step 122, the computer 30 searches the two dimensional x-ray projections 208 to determine the actual position of each CT marker 60 in the two dimensional x-ray projections 208. As the anatomy of the patient P is suppressed, the anatomy has little effect on the search. Data collected in step 112 about the positions of the markers 60 can also be used to help determine the positions of the markers 60 in the two dimensional x-ray projections 208.

In step 124, the computer 30 employs a software routine to estimate the pose of the head of the patient P consistent with the actual projected positions of the markers 60 as measured in step 122. The computer 30 may do this, for example, using a non-linear least squares regression routine. If the spacings between the markers 60 are known, the software routine may exploit this information. This may be the case, for example, if the head gear 90 is constructed rigidly so that the spacings between the markers 60 are fixed and non-deformable. The spacings between the markers 60 can then be measured in a preliminary CT scan of the head gear 90 alone. Otherwise, the software routine can treat the spacings between the markers 60 as additional unknowns and estimate them along with the pose of the head. The result of this analysis provides a motion data set.

In step 130, the computer 30 employs a software routine to reconstruct a final three dimensional CT image employing the two dimensional x-ray projections 200 and the motion data set. The software routine accounts for motion of the patient P as identified in the motion data set to create a higher quality three dimensional CT image.

The method can be repeated to create a progressively better motion data set and improved motion corrected images. In each iteration, the motion data set determined in step 128 is saved and then incorporated in the next iteration.

The foregoing description is only exemplary of the principles of the invention. Many modifications and variations of the present invention are possible in light of the above teachings. The preferred embodiments of this invention have been disclosed, however, so that one of ordinary skill in the art would recognize that certain modifications would come within the scope of this invention. It is, therefore, to be understood that within the scope of the appended claims, the invention may be practiced otherwise than as specifically described. For that reason the following claims should be studied to determine the true scope and content of this invention.

What is claimed is:

1. A method of correcting for motion of a patient during a CT scan, the method comprising the steps of:
   a) positioning a plurality of radio-dense or radio-opaque markers on a patient;
   b) measuring actual projected positions of the plurality of markers in each two dimensional x-ray projection collected by a CT scanner;
   c) obtaining a motion data set based on measurements obtained in said step b); and
   d) reconstructing a final three dimensional CT image employing the motion data set.

2. The method as recited in claim 1 wherein said step c) is performed using a software routine that estimates both rigid spacings between the plurality of markers on the patient together with a variation in position and orientation of a marker configuration throughout a CT scan.

3. The method as recited in claim 1 wherein said step a) is performed using a head gear that is deformable to fit the heads of different patients.

4. The method as recited in claim 1 wherein, in said step a), spacings between the plurality of markers once attached to the patient are known, and the spacings are used to facilitate said step c).

5. The method as recited in claim 1 wherein said step b) includes
   b1) reconstructing a three dimensional CT image;
   b2) determining a spatial location of each of the plurality of markers in the three dimensional CT image;
   b3) storing information about the spatial location of each of the plurality of markers;
   b4) deleting the plurality of markers from the three dimensional CT image to generate a new three dimensional CT image;
   b5) generating a set of simulated two dimensional x-ray projections from the new three dimensional CT image; and
   b6) subtracting the set of simulated two dimensional x-ray projections from the plurality of two dimensional x-ray projections to produce a new set of two dimensional x-ray projections showing the plurality of markers.

6. The method as recited in claim 5 including said step of:
   b7) using information collected in said step b3) to help locate the markers in the measured two dimensional x-ray projections.

7. The method as recited in claim 1 including a gantry that houses an x-ray source that generates x-rays and a detector that converts the x-rays to the plurality of two dimensional x-ray projections, including the step of rotating the gantry about an axis of rotation.

8. The method as recited in claim 1 wherein the plurality of markers are a ball bearing or a BB.

9. The method as recited in claim 1 wherein the plurality of markers include at least three markers.

10. A method of correcting for motion of a patient during a CT scan, the method comprising the steps of:
    a) positioning a plurality of radio-dense or radio-opaque markers on a patient;
    b) obtaining a plurality of two dimensional x-ray projections of the patient;
    c) generating a three dimensional CT image from the plurality of two dimensional x-ray projections;
    d) determining a location of each of the plurality of markers in the three dimensional CT image;
    e) deleting the plurality of markers from the three dimensional CT image to generate a new three dimensional CT image;

f) generating a set of simulated two dimensional x-ray projections from the new three dimensional CT image;

g) subtracting the set of simulated two dimensional x-ray projections from the plurality of two dimensional x-ray projections to produce a new set of two dimensional x-ray projections showing the plurality of markers;

h) determining an actual projected position of each of the plurality of markers in the new set of two dimensional x-ray projections;

i) obtaining a motion data set based on a known spacing and an orientation of the plurality of markers and the actual projected position of each of the plurality of the markers; and j) reconstructing a final three dimensional CT image employing the motion data set.

11. The method as recited in claim 10 including the step of:
k) determining the spacing and the orientation of the plurality of markers, wherein the plurality of markers have a fixed and rigid relationship.

12. The method as recited in claim 11 wherein said step k) occurs before said steps a) through j).

13. The method as recited in claim 10 wherein said step k) includes performing a CT scan of an object including the plurality of markers to determine the spacing and the orientation of the plurality of markers.

14. The method as recited in claim 13 wherein the object is a head gear.

15. The method as recited in claim 11 wherein said steps c) through j) are repeated, and the motion data set obtained from said step i) is saved and employed in a next iteration.

16. The method as recited in claim 10 including a gantry that houses an x-ray source that generates x-rays and a detector that converts the x-rays to the plurality of two dimensional x-ray projections, including the step of rotating the gantry about an axis of rotation.

17. The method as recited in claim 10 including said step of:
k) storing information about the location of each of the plurality of markers obtained from said step d).

18. The method as recited in claim 10 wherein the plurality of markers are a ball bearing or a BB.

19. The method as recited in claim 10 wherein the plurality of markers include at least three markers.

20. A method of correcting for motion of a patient during a CT scan, the method comprising the steps of:
a) positioning a plurality of radio-dense or radio-opaque markers on a patient;
b) deriving a three dimensional CT image from two dimensional x-ray projections collected during a CT scan;
c) employing the three dimensional CT image to determine an actual position of each of the plurality of markers in each two dimensional x-ray projection of the patient;
d) obtaining a motion data set based on the actual position of the plurality of the markers in each two dimensional x-ray projection; and
e) reconstructing a final three dimensional CT image employing the motion data set.

21. The method as recited in claim 20 wherein said steps b) through e) are repeated, and the motion data set obtained from said step d) is saved and employed in a next iteration.

22. A CT scanner comprising:
a gantry including a first arm and a second arm;
an x-ray source that generates x-rays, wherein one of the first arm and the second arm houses the x-ray source;
a detector that converts the x-rays to a plurality of two dimensional x-ray projections, wherein the detector is housed in the other of the first arm and the second arm; and
a computer for correcting for motion of a patient during a CT scan, wherein the computer generates a three dimensional CT image from the plurality of two dimensional x-ray projections, determines an actual projected position of each of a plurality of markers positioned on the patient, obtains a motion data set based on the actual projected positions of the plurality of the markers, and reconstructs a final three dimensional CT image employing the motion data set.

23. The CT scanner as recited in claim 22 wherein the gantry is rotatable about an axis of rotation.

24. The CT scanner as recited in claim 22 wherein the plurality of markers are a ball bearing or a BB.

25. The CT scanner as recited in claim 22 wherein the plurality of markers include at least three markers.

26. The CT scanner as recited in claim 22 wherein the plurality of markers are located on a head gear.

27. A CT scanner comprising:
a gantry including a first arm and a second arm;
an x-ray source that generates x-rays, wherein one of the first arm and the second arm houses the x-ray source;
a detector that converts the x-rays to a plurality of two dimensional x-ray projections, wherein the detector is housed in the other of the first arm and the second arm; and
a computer for correcting for motion of a patient during a CT scan, wherein the computer generates a three dimensional CT image from the plurality of two dimensional x-ray projections, determines a location of each of a plurality of markers in the three dimensional CT image, deletes the plurality of markers from the three dimensional CT image to generate a new three dimensional CT image, generates a set of simulated two dimensional x-ray projections from the new three dimensional CT image, subtracts the set of simulated two dimensional x-ray projections from the two dimensional x-ray projections to produce a new set of two dimensional x-ray projections showing the plurality of markers, determines an actual projected position of each of the plurality of markers in the new set of two dimensional x-ray projections, obtains a motion data set based on the actual projected positions of the plurality of the markers, and reconstructs a final three dimensional CT image employing the motion data set.

28. The CT scanner as recited in claim 27 wherein the gantry is rotatable about an axis of rotation.

29. The CT scanner as recited in claim 27 wherein the plurality of markers are a ball bearing or a BB.

30. The CT scanner as recited in claim 27 wherein the plurality of markers include at least three markers.

31. The CT scanner as recited in claim 27 wherein the plurality of markers are located on a head gear.

* * * * *